United States Patent [19]
Fletcher et al.

[11] 3,995,621
[45] Dec. 7, 1976

[54] LIQUID COOLED BRASSIERE AND METHOD OF DIAGNOSING MALIGNANT TUMORS THEREWITH

[76] Inventors: James C. Fletcher, Administrator of the National Aeronautics and Space Administration, with respect to an invention of William Elkins, San Jose; Bill Alvin Williams, Morgan Hill; Ernest Glenn Tickner, Mountain View, all of Calif.

[22] Filed: Jan. 27, 1976

[21] Appl. No.: 652,948

[52] U.S. Cl. .............................. 128/2 H; 128/379; 128/400; 128/402
[51] Int. Cl.² ...................... A61B 5/06; A61F 7/00
[58] Field of Search .......... 128/2 A, 2 H, 2 R, 399, 128/400, 402, 379, 384

[56] References Cited
UNITED STATES PATENTS

| | | | |
|---|---|---|---|
| 500,568 | 7/1893 | Ells | 128/402 X |
| 546,436 | 9/1895 | Springstein | 128/402 X |
| 3,500,832 | 3/1970 | Munnery | 128/379 |
| 3,830,224 | 8/1974 | Vanzetti et al. | 128/2 H |
| 3,842,802 | 10/1974 | Lang et al. | 128/2 H |
| 3,847,139 | 11/1974 | Flam | 128/2 H |

*Primary Examiner*—Lawrence W. Trapp
*Attorney, Agent, or Firm*—Darrell G. Brekke; Gary F. Grafel; John R. Manning

[57] ABSTRACT

A device for enhancing the detection of malignant tissue in the breasts of a woman comprises a brassiere-like garment which is fitted with a pair of liquid-perfused cooling panels which completely and compliantly cover the breasts and upper torso. The garment is connected by plastic tubing to a liquid cooling system comprising a fluid pump, a solenoid control valve for controlling the flow of fluid to either the cooling unit or the heating unit, a fluid reservoir, a temperature sensor in the reservoir, and a restrictor valve to control the pressure in the garment inlet cooling line.

12 Claims, 4 Drawing Figures

LIQUID COOLED BRASSIERE AND METHOD OF DIAGNOSING MALIGNANT TUMORS THEREWITH

ORIGIN

The invention described herein was made in the performance of work under a NASA contract and is subject to the provisions of Section 305 of the National Aeronautics and Space Act of 1958, Public Law 85–568 (72 Stat. 435; 42 U.S.C. 2457).

BACKGROUND OF THE INVENTION

1. Field of the Invention

The present invention relates generally to a device and method for the detection of breast tumors in women comprising cooling the tissues of the breast and then scanning the temperature patterns with thermographic techniques. More particularly, the invention relates to a breast cooling device for enchancing the detection of breast cancer comprising liquid-perfused cooling patches, means for pumping liquid through the patches and means for controlling the temperature of the cooling liquid.

2. Description of the Prior Art

In the past, a limited number of devices and methods have been described for measuring or sensing the temperature of various tissues, such as the skin temperature, in order to determine the presence of cancerous tissue. It is well established that the temperature of the skin in the vicinity of a tumor, such as a cancerous tumor, is significantly higher than the temperature of normal skin tissue located in the same or similar body area. The higher temperature is due largely to a greater perfusion of warm blood in the area of the tumor compared to perfusion in the non-tumorous area.

One such type of prior art device comprises an item of clothing to be worn over the skin, the item including a suitable distribution of packages comprising liquid crystals responsive to changes in skin temperature. In this type of prior art device, the package for the liquid crystals may be in the form of a circular or elongated laminar package. Or, the liquid crystals can be incorporated in cavities within a plastic sheet or rod. In one embodiment, the liquid crystals are encapsulated and the capsules incorporated in the textile fibers which are used for making body garments such as brassieres. The liquid crystals in each cavity or capsule may be selected to be operative in different temperature ranges, such as between 95° to 97° F., 97° to 99° F., etc. Temperature gradients on the skin of a person are made visible by placing liquid crystals, whether in the form of packages, fibers of encapsulated liquid crystals, or garments made of such fibers, on or near any desired area of a person's body. An example of the above described use of liquid crystals is found in U.S. Pat. No. 3,830,224.

Yet another use of liquid crystals for sensing the temperature of the skin of a person is described in U.S. Pat. No. 3,847,139 where liquid crystals are coated onto the inside surface of a conformable textile brassiere to provide a visible indication of the skin temperature. In this embodiment, the liquid crystals, either in free solution or as a dispersion of encapsulated liquid crystals, are sprayed onto the inner surface of the textile garment.

Yet another device and method for diagnostic thermography is shown in U.S. Pat. No. 3,335,716. In this prior art invention, the body is coated with a phosphor which luminesces when excited with ultraviolet light. the degree of luminescence is inversely proportional to the temperature of the underlying tissue. The temperature gradient of the body is monitored with a television camera and displayed on a picture tube.

Another type of device for measuring the temperature of small areas of skin tissue is shown in U.S. Pat. No. 3,877,463. In this embodiment, the perfusion rate of superficial skin tissue is used as an aid in diagnosing the presence or absence of tumors. The determination is carried out by cooling a small area of normal tissue and of suspected malignant tissue through a thermal resistance of known value and measuring the the temperature difference between the two readings. The cooling device is manufactured in the shape of a small cylinder (about 1 inch diameter) and comprises a flat heat collecting disc, heat sink means, cooling means, and thermocouple sensing means.

SUMMARY OF THE INVENTION

A primary object of the invention is to provide a device and method for enhancing the detection of malignant tissue in the breast of a woman.

Another object of the present invention is to provide a device for the early detection of breast cancer in women which comprises a compliant body conforming garment in the nature of a brassiere designed to cover the upper torso and breasts of a patient with a pair of liquid-perfused cooling patches or panels for evenly and uniformly cooling this region of the body prior to obtaining an infrared scan of the cooled region. Each liquid-perfused cooling panel is conformably attached to the interior surface of each cup of the brassiere.

A major object of the present invention is to provide a convenient, comfortable and inexpensive device for cooling the skin tissue of the breast and thoracic regions of a patient to a uniform temperature prior to scanning the temperature patterns with thermographic techniques.

The preferred embodiment of the present invention comprises a brassiere-like garment made of body conforming material including a pair of body compliant liquid-perfused cooling panels lying adjacent and held within the inner contour of each cup with suitable attaching means such as snaps, sewing, etc., a pump connected by flexible tubing to the liquid-perfused cooling panels, a solenoid valve for controlling the flow of cooling liquid between the pump and the refrigerator-heat exchanger and heaters, a refrigerator-heat exchanger for cooling the cooling fluid, a heater for heating the cooling fluid, a cooling fluid reservoir tank, an temperature sensor located in the reservoir tank for sensing the cooling fluid temperature and a temperature readout and controller circuit for controlling the solenoid valve and heater circuit.

An important advantage of the present invention over prior art is that it provides uniform cooling and temperature control of the entire breast area simultaneously.

Another advantage of the present invention is that it provides means for adjusting the temperature of the entire breast area to precise pre-determined levels.

These and other objects and advantages will become apparent from a reading of the following detailed description of the preferred embodiments which are illustrated in the figures in the drawings.

DETAILED DESCRIPTION OF THE INVENTION

Figure 1:
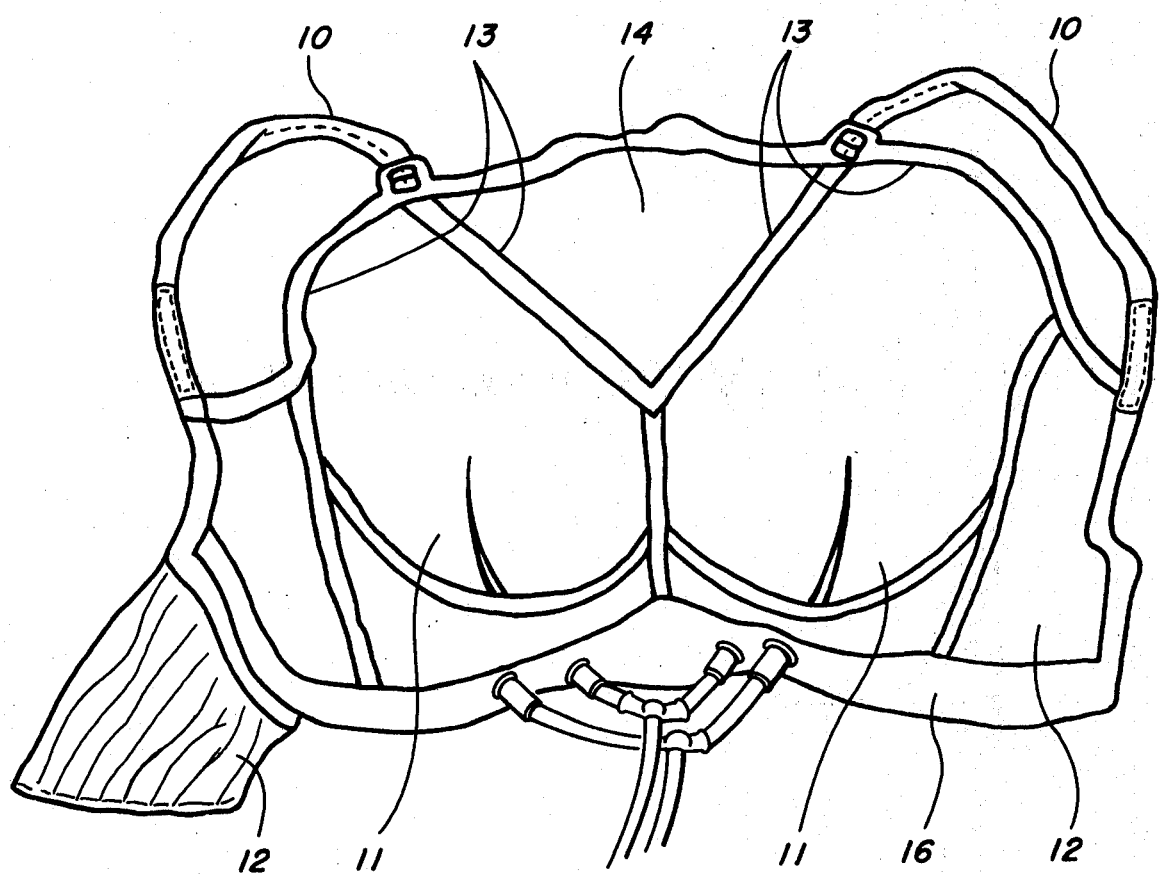
FIG. 1 is a front perspective view of the body conforming garment portion of the present device.

Referring now to FIG. 1 of the drawing, there is shown illustrated generally at 16 the body conforming garment made in accordance with the present invention. Garment 16 is designed to cover the upper torso and breasts of a person and is usually referred to as a brassiere. Garment 16 comprises cup portions 11 for positioning over the breasts and support means represented by shoulder straps 10 for supporting garment 16 in its proper position in relation to the breasts. Shoulder straps 10 include a buckle for adjusting the length of the straps. Straps 10 extend from the upper portion of cups 11 and over the shoulders to the back portion 12 of garment 16. The tops and sides of cups 11 are reinforced with straps 13. In order to maximize conformation of cups 11 over the person's breasts an extra panel of stretchable elastic material 14 is included over the sternum between reinforcing straps 13.

Figure 2:
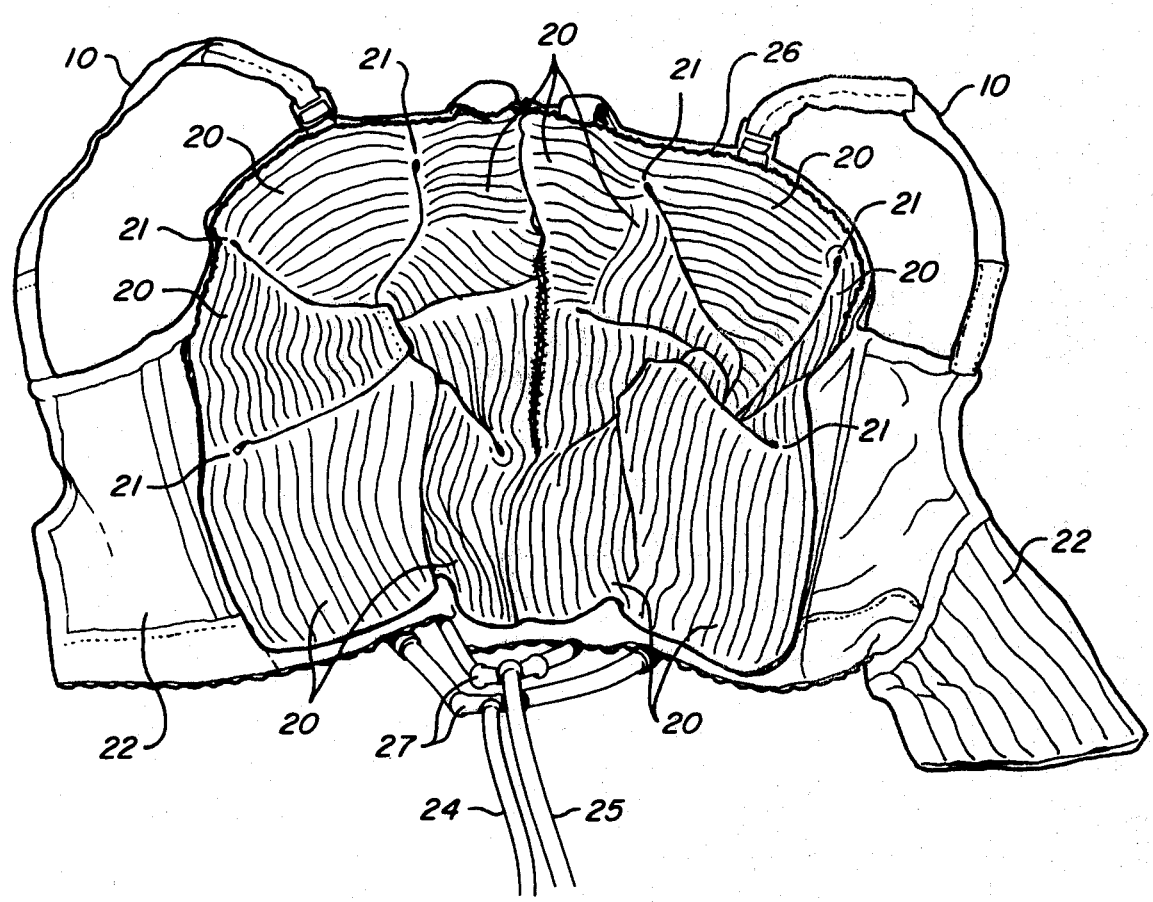
FIG. 2 is a perspective view of the back of the body conforming garment showing the liquid-perfused cooling panels or patches disposed within the cups of the garment.

Referring to FIG. 2, there is illustrated the body contacting side of the breast cooling means of the invention. As can be seen from the illustration, the preferred cooling means is in the form of a garment generally known as a brassiere comprising a pair of liquid-perfused cooling panels attached by suitable means, such as by sewing, shown at 26, to the inner surface of the brassiere. Each liquid-perfused cooling panel includes a multiplicity of individual sections 20 which are in the shape of Mercator projections which conform generally to the contour of the breast when fitted and coupled with the interior of the brassiere. Each cooling panel is connected to cooling liquid inlet line 24 and to cooling liquid outlet line 25 through a connecting Y coupler 26. Connecting channels or manifolds 21 form a continuous flow path through each cooling panel and permit perfusion of cooling fluid throughout each section 20 of the cooling panel while at the same time allow sufficient flexibility of the cooling panel for a biconcave fit into the brassiere cups. The brassiere is designed to permit complete coverage of the breast area and allows for freedom of cup movement for conformation to breast shape. Backstraps 22 are fastened together by suitable means to hold and conform the brassiere to the torso. Preferably, backstraps 22 are provided with releasable fastening means such as Velcro material. For that purpose, Velcro material is attached to opposing sides of backstraps 22 and pressed together to make the connection.

Figure 3:
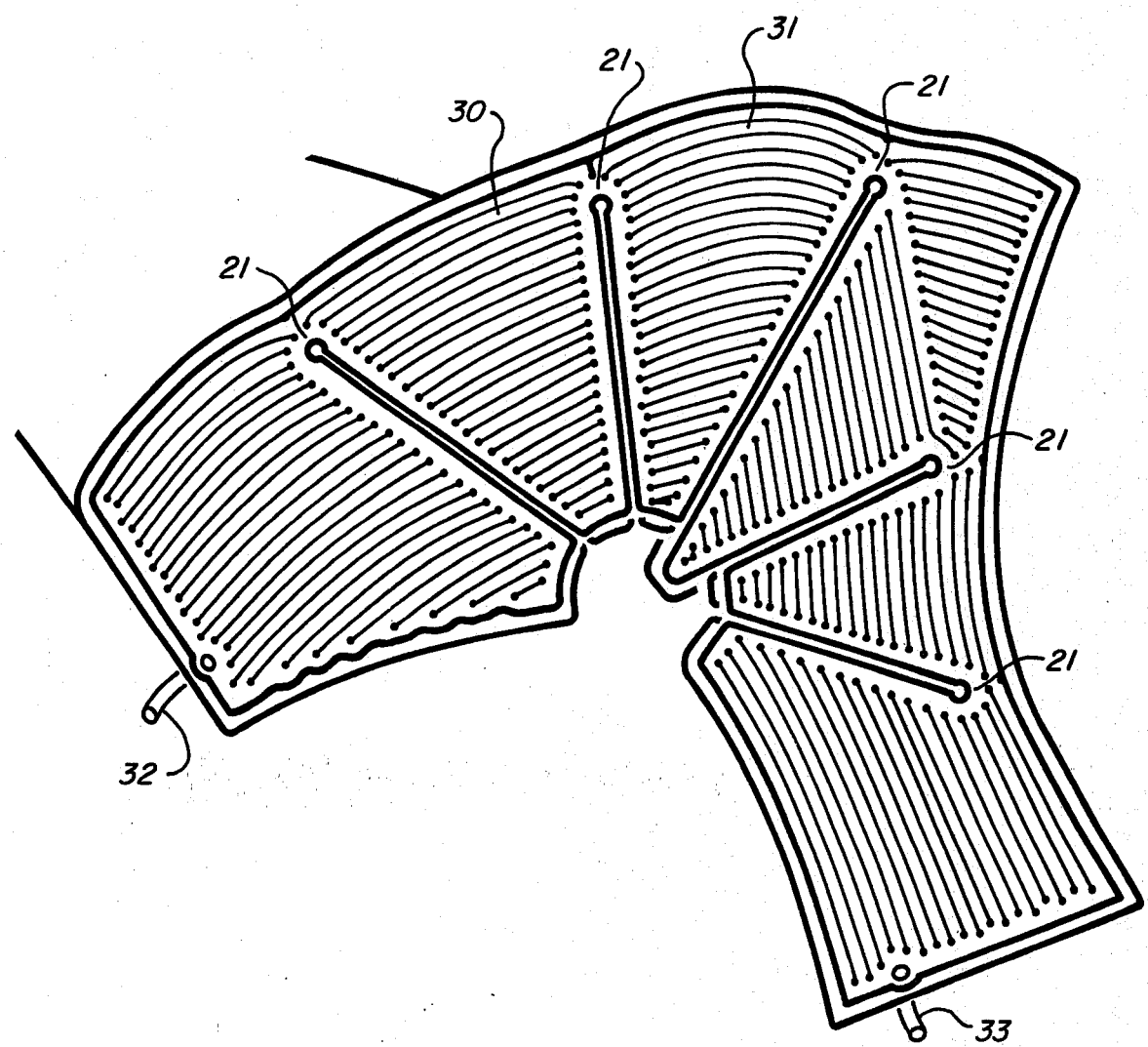
FIG. 3 is a plan view of the liquid-perfused panel constructed in accordance with the invention.

FIG. 3 illustrates the design and planar configuration of the liquid-perfused cooling panel of the invention. This view shows the cooling panel before folding and fitting into each cup of the brassiere. In the preferred embodiment of FIG. 3, the cooling panel includes six sections, all of which are connected by a free flow manifold 21. A method for making the preferred cooling panels of this invention is disclosed in U.S. Pat. No. 3,830,676 and in U.S. patent application Ser. No. 553,030, filed Feb. 25, 1975 and entitled "Liquid Cooled helmet" In general, these cooling panels are made of two superposed sheets of flexible waterproof material such as rubber, polyurethane, fabric coated with elastomeric material and sealing the sheets such as by vulcanizing or heat-sealing at the edges and along spaced apart lines 31 to form the desired pattern and liquid cooling passageways 30. Inlet tube 32 and outlet tube 33 are connected to the outlet cooling line 25 and the inlet cooling line 24, respectively, of FIG. 2. The design of the preferred cooling panel of FIG. 3 is such that it is readily attached to the brassiere simply by folding and fitting a panel in each cup of the brassiere and sewing the outer edges of the panels to the brassiere.

Figure 4:
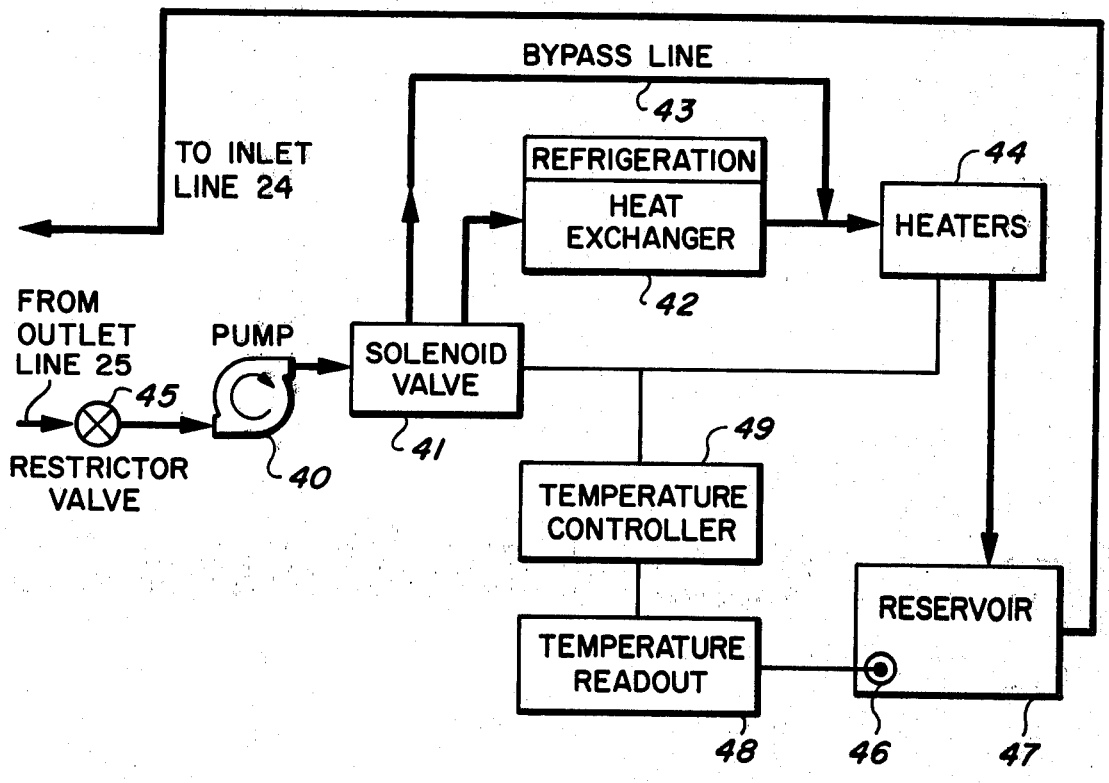
FIG. 4 is a schematic diagram illustrating the cooling, pumping and temperature control systems constructed according to the present invention.

Referring to FIG. 4, there is shown a schematic illustration of the pumping, cooling and temperature control means for use with the liquid cooled brassiere of the invention. The pumping system comprises pumping means 40 which, preferably, is a water pump, having sufficient capacity to produce flow rates of 0.5 gallons/minute with a pressure head in excess of 20 psig. A suitable commercially available pump, for example, is the Model 12-64-303, 117 volt, manufactured by Micropump Company. The cooling fluid from pump 40 flows under a pressure of 10 psig. to 30 psig. to solenoid valve 41 and there the flow is routed either through bypass line 43 or through refrigeration unit 42. If the temperature of the cooling fluid is above a desired temperature, solenoid valve 41 will direct the stream of cooling fluid through refrigeration unit 42; if the temperature is below the desired temperature the solenoid valve 41 will direct the flow through bypass line 43. Heating means 44 receives the cooling fluid from either bypass line 43 or refrigeration unit 42. After being heated to the proper temperature by heating means 44, the cooling fluid flows to reservoir 47, then into inlet line 24 of the brassiere, as shown in FIG. 2. Restrictor valve 45 placed prior to the pump 40 inlet assures that the desired pressure to maintained in the cooling line to the brassiere. Refrigeration unit 42 preferably will have over 1000 BTU/hr. cooling capacity. A typical unit, for example, is Model HRC-4 manufactured by Haws Refrigeration Company. Heating means 44 preferably has a heating capacity of 400–500 BTU/hr. A heater commercially available from Briskeat Company is suitable for the purposes of the invention.

Since the temperature of the cooling fluid must be controlled within narrow limits, the temperature control system is extremely important. The thermal control system comprises temperature sensing means 46, which may be a thermocouple, temperature readout 48 and temperature controller 49. Temperature is controlled by an analog temperature controller such as the Love Controls Corporation Model 48–837.Temperature control is within ± 0.5° C. using this device.

Sensor 46 is situated in reservoir 47 and senses any change in the temperature of the cooling fluid. A change in the temperature generates a signal in sensor 46 which is sensed by temperature readout 48 and temperature controller 49. In turn, controller 49 controls the on-off status of heating means 44 and the action of solenoid valve 41. If the temperature of the cooling fluid is below the desired temperature, solenoid valve 41 directs the flow of cooling fluid through bypass line 43.

The liquid-cooled brassiere and its associated pumping-thermal control system is preferably used in the following manner: The patient dons the brassiere and adjusts the support straps for maximum skin tissue coverage, comfort and fit. Brassiere purfusant tubing, inlet tube 24 and outlet tube 25 in FIG. 2, is connected to the pumping-thermal control system and the system energized to start the flow of water, the preferred cooling fluid, within the system. The desired cooling fluid or brassiere panel temperature is then set on the temperature controller and the ensuing combination of chilling-cooling sequences brings the perfusant water temperature to the desired low skin temperature. Generally, it is desirable to lower the skin temperature to 15° C. in order to ensure complete local vasoconstriction.

After the patient's breasts have been uniformly cooled to the desired temperature, the liquid-cooled brassiere is removed and an infrared thermographic scan is begun. For this purpose a Spectroscan 2000 infrared scanner can be used.

Thermographic scan techniques are well known and will not be described further herein. Sequential theremographic photographs or video tapes will show not only skin discontinuities in skin temperature overlying malignant tumor areas (warmer), but will also depict time transient recovery responses. Diseased areas not large enough or close enough to the skin surface to appear in the normal infrared scan may appear as alterations in transients of recovery temperature. What is claimed is:

1. A device for enhancing the detection of cancer in the breasts of a women comprising:
   a breast and upper torso conforming garment comprising means for uniformly and simultaneously cooling the skin tissue of said breast by the perfusion of cooling fluid through said cooling means;
   means for controlling the temperature of said cooling fluid;
   means for refrigeration of said cooling fluid;
   means responsive to said controlling means for heating said cooling fluid;
   a reservoir for holding said cooling fluid;
   valve means responsive to said controlling means for controlling the flow of cooling fluid between said refrigeration means and said heating means;
   means for pressurizing and circulating said cooling fluid through said refrigeration means, heater means, valve means, fluid reservoir, and garment cooling means.

2. The device of claim 1 wherein the conforming garment is a brassiere.

3. The device of claim 2 wherein said conforming garment cooling means includes a pair of liquid-perfused cooling panels conformably connected to the interior surface of each cup of said brassiere with suitable attaching means.

4. The device of claim 3 wherein the said liquid-perfused cooling panels comprise two sheets of flexible waterproof material joined together to form a plurality of passageways for carrying a cooling fluid, and inlet and outlet flow lines connected to the panels and communicating with the passageways for carrying the cooling liquid to and from the said passageways.

5. A device as in claim 3 wherein the means for pressurizing and circulating includes a water pump having a capacity of at least 0.5 gallons per minute and a restrictor valve for maintaining a desired pressure.

6. A device as in claim 3 wherein the means for refrigeration is a heat-exchanger having a capacity of at least 100 BTU/hr. cooling capacity.

7. A device as in claim 3 wherein the heating means is a water heater having a capacity of at least 400 BTU/hr.

8. A device as in claim 3 wherein the means for controlling the temperature includes a temperature sensor and an analog temperature controller.

9. A device as in claim 8 wherein the sensor is a thermocouple located in the cooling fluid reservoir.

10. The device of claim 3 wherein the cooling fluid is water.

11. The method of enhancing the detection of breast cancer in a woman comprising the steps of:
    a. cooling the skin tissue of a woman's breasts below normal room temperature by placing the breasts in close contact with a conforming garment comprising liquid-perfused cooling panels, said panels maintained at said temperature by the flow of cooling fluid therein;
    b. removing the conforming garment; and
    c. scanning the thermal pattern of the skin with an infrared scanning device.

12. The method of claim 11 wherein the temperature of the skin tissue is cooled to about 15° C.

* * * * *